United States Patent
Brazdeikis et al.

(10) Patent No.: US 9,167,983 B2
(45) Date of Patent: Oct. 27, 2015

(54) IMAGING METHOD FOR OBTAINING SPATIAL DISTRIBUTION OF NANOPARTICLES IN THE BODY

(75) Inventors: Audrius Brazdeikis, Missouri City, TX (US); Subhasis Sarangi, Houston, TX (US)

(73) Assignee: THE UNIVERSITY of Houston System, Houston, TX (US)

(*) Notice: Subject to any disclaimer, the term of this patent is extended or adjusted under 35 U.S.C. 154(b) by 962 days.

(21) Appl. No.: 12/541,083

(22) Filed: Aug. 13, 2009

(65) Prior Publication Data

US 2010/0066363 A1   Mar. 18, 2010

Related U.S. Application Data

(60) Provisional application No. 61/089,356, filed on Aug. 15, 2008.

(51) Int. Cl.
 *A61B 5/05* (2006.01)
(52) U.S. Cl.
 CPC ............... *A61B 5/05* (2013.01); *A61B 5/0515* (2013.01)
(58) Field of Classification Search
 CPC .................................. A61B 5/0515; A61B 5/05
 See application file for complete search history.

(56) References Cited

U.S. PATENT DOCUMENTS

| | | | |
|---|---|---|---|
| 6,027,946 A * | 2/2000 | Weitschies et al. | 436/526 |
| 2003/0085703 A1* | 5/2003 | Gleich | 324/309 |
| 2004/0027125 A1* | 2/2004 | Clarke et al. | 324/308 |
| 2007/0232899 A1* | 10/2007 | Bill et al. | 600/424 |

FOREIGN PATENT DOCUMENTS

WO   WO 2006035359 A2 *   4/2006   ............... A61B 5/05

OTHER PUBLICATIONS

Gleich et al., Tomographic imaging using the nonlinear response of magnetic particles, Nature, vol. 435/30, Jun. 2005, pp. 1214 to 1217.*
Special report: magnetic nanoparticles, Aug. 9, 2006, http://www.magneticmicrosphere.com/archive/images/Gould__magnetic%20nanoparticles_MedicalPhysicsWeb_090806.pdf.*
Schambach et al., SQUID Gradiometer Measurement System for Magnetorelaxometry in a Disturbed Environment, IEEE Transactions on Applied Superconductivity, vol. 9, No. 2, Jun. 1999, p. 3527-3530.*
Gleich et al., Magnetic Particle Imaging (MPI), MEDICAMUNDI, 50/1, May 2006, p. 66-71.*
Ludwig et al., Characterization of superparamagnetic nanoparticles by analyzing the magnetization and relaxation dynamics using fluxgate magnetometers, Journal of Applied Physics 101, 113909, 2007, published online Jun. 6, 2007.*

* cited by examiner

*Primary Examiner* — Bo J Peng
(74) *Attorney, Agent, or Firm* — Robert W Strozier (57) ABSTRACT

A well-posed magnetic imaging method is disclosed that exploits the non-linear behavior of the characteristic time scale of the Néel relaxation for obtaining accurate high-spatial resolution images of magnetic tracers. The method includes placing an object in a selection field (static field) generated by three pairs of orthogonally arranged coil (drive coils), supplying prudently choice currents to the drive coils, a zero field voxel (ZFV) is formed that can be positioned anywhere in the local region of interest (ROI), switching the magnetizing field off, and collecting an image.

12 Claims, 8 Drawing Sheets

FIG. 2B
(Top view)

IMAGING METHOD FOR OBTAINING SPATIAL DISTRIBUTION OF NANOPARTICLES IN THE BODY

RELATED APPLICATIONS

This application claims priority to and the benefit of U.S. Provisional Patent Application Ser. No. 61/089,356, filed 15 Aug. 2008 (Aug. 15, 2008).

BACKGROUND OF THE INVENTION

1. Field of the Invention

The present invention relates to a method for well-posed magnetic imaging.

More particularly, the present invention relates to a well-posed magnetic imaging method that exploits a non-linear behavior of a characteristic time scale of the Néel relaxation for obtaining accurate high-spatial resolution images of magnetic tracers. The present invention also relates to new medical diagnostic instruments for characterization and imaging of vulnerable plaque.

2. Description of the Related Art

Magnetic relaxation of microscopic amounts of magnetic nanoparticles after switching off a magnetizing field can be measured very accurately using a superconducting quantum interference device (SQUID), the most sensitive and stable magnetic flux sensor. Weitschies et al. proposed magnetic relaxation immunoassay based on the magnetic relaxation of functionalized magnetic nanoparticles (MNP), where MNPs bound to biological targets (e.g., antibody, tissue, microorganisms etc.) were distinguished from unbound particles based on different relaxation times. The magnetic relaxation (MRX) technique has the advantages over other conventional techniques of being specific, quantitative, and sensitive in distinguishing between bound and unbound magnetic labels. This fact permits the use of a homogeneous assay, which does not require separation and removal of unbound MNPs. This technique has been extended for detection of magnetotactic bacteria, binding kinetics, cancer diagnosis, magnetically labeled immunoassay, drug localization, transplant rejection detection, hydrogel characterization, and dissipative heating in ferrofluids. By using a model system of liposomes, Chemla et al. demonstrated that the technique is sensitive enough to detect $5 \times 10^4$ nanoparticles by a SQUID sensor and discussed the possibility of obtaining a detection limit of 50-500 MNPs The general theory of using MRX for imaging application was first proposed by Warzemann et al. and recently explored by others. But their approaches are practically restricted to a 2D image registration and have poor spatial resolution due to an inverse problem associated with transforming the data into a spatial image. Thus, there is a need in the art for a new direct magnetic relaxation imaging technique that exploits the non-linear behavior of the characteristic time scale of the Néel relaxation.

SUMMARY OF THE INVENTION

The present invention provides a well-posed magnetic imaging method and instruments using the method, which exploits the non-linear behavior of a characteristic time scale of the Néel relaxation to obtain accurate, high-spatially resolved images of magnetic tracers. To record an image using this new technique, an object, body (living organism) or part thereof is placed in a selection magnetic field (static magnetic field) generated, in certain embodiments, by three pairs of coil (drive coils) orthogonally oriented with respect to each other. By a prudent choice of the current supplied to the drive coils, a zero field voxel (ZFV) is formed. The ZFV can be positioned anywhere in a region of interest (ROD within the body (living organism), object or part thereof. After the selection magnetic field or magnetizing field having a strength Hmag is switched off, MNPs located outside the ZFV relax in a finite field (H>0), so their magnetization decays rapidly within a few milliseconds (ms) and make no or substantially no measurable contribution to a measured signal or an image of the ROI or ROIs within the ZFV. For any MNPs located within the ZFV, their magnetization decay rate is slower and make all or substantially all the contributions to the measured signal or image. The ZFV can be focused and/or positioned very accurately over an ROI either using mechanical scanning or by changing currents supplied to the drive field coils. Additionally, both methods can be combined to position the ZFV over a desired ROI. The mechanical scanning is performed by moving the whole drive coil assembly relative to the body (living organism), object or part thereto or by moving the body (living organism), object or part thereof within the drive coil assembly. A 2D or 3D tomographic image of a magnetic tracer distribution in the ROI is directly obtained by mapping magnetization decays measured by a sensitive magnetic field sensor.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that a new imaging device and a new method for imaging can be constructed using magnetic relaxometry, where a relaxation of a magnetic moments of a magnetic nanoparticles (MNPs) after being aligned by a magnetic field pulse depends on a particle size of the MNPs and on whether the MNPs are bound. We have developed a comprehensive description and experimental demonstration of a novel magnetic relaxation imaging method and instrument using superparamagnetic tracers. The advantage over stray field imaging is that the spatial resolution is not limited by a pick-up coil size or a sample-to-sensor distance.

Concept

The basic concept of magnetic relaxometry is that a relaxation of a magnetic moment of a MNP, after being aligned by a magnetic field pulse, depends on a MNP particle size and on whether the MNP is bound. A sample including MNPs is exposed to a magnetic field having an amplitude $H_{mag}$ for a time $t_{mag}$. After the polarizing or aligning magnetic field is switched off, a remnant magnetization decays (relaxes) as an alignment of magnetic moments reverts back to chaos or a random distribution, either by Brownian motion, typically in microseconds, or, if the particles are immobilized or bound and cannot rotate freely, by the Néel relaxation mechanism, in milliseconds or longer depending on the size of the MNP. If Brownian relaxation is suppressed, e.g., the particles are blocked or hindered in their mobility as a result being bound to a target molecule, only Néel relaxation is possible. The net relaxation of these bound magnetic particles can be phenomenologically described by equation (1):

$$B_r(t) = B_N \int_0^\infty P(r)L(r,H) \times \left\{1 - \exp\left[\frac{-t_{mag}}{\tau_N(H_{mag})}\right]\right\} \times \left\{\exp\left[\frac{-t}{\tau_N(H)}\right]\right\} dr \quad (1)$$

where $B_r$ is the remanence field, $B_N$ is the magnetic field produced by the magnetic particles just before relaxation, $P(r)$ is the particle size distribution, and $L(r,H)$ is the Langevin function.

The time constant of Néel relaxation $\tau_N$ in a magnetic field of strength H for a system of non interacting magnetic particles with an anisotropic field $H_k$ is given by equation (2):

$$\tau_N(H) = \tau_0 \exp\left[\frac{KV(1-h)^2}{kT}\right] \quad (2)$$

where $\tau_0$ is a constant and usually quoted as $10^{-9}$ s, K is the anisotropy energy constant, V is the volume, k is the Boltzman constant, T is the absolute temperature, and $h=H/H_k$. In zero field (H=0), the expression for the Néel relaxation time reduces to equation (3):

$$\tau_N = \tau_0 \exp[KV/kT] \quad (3)$$

Figure 1:
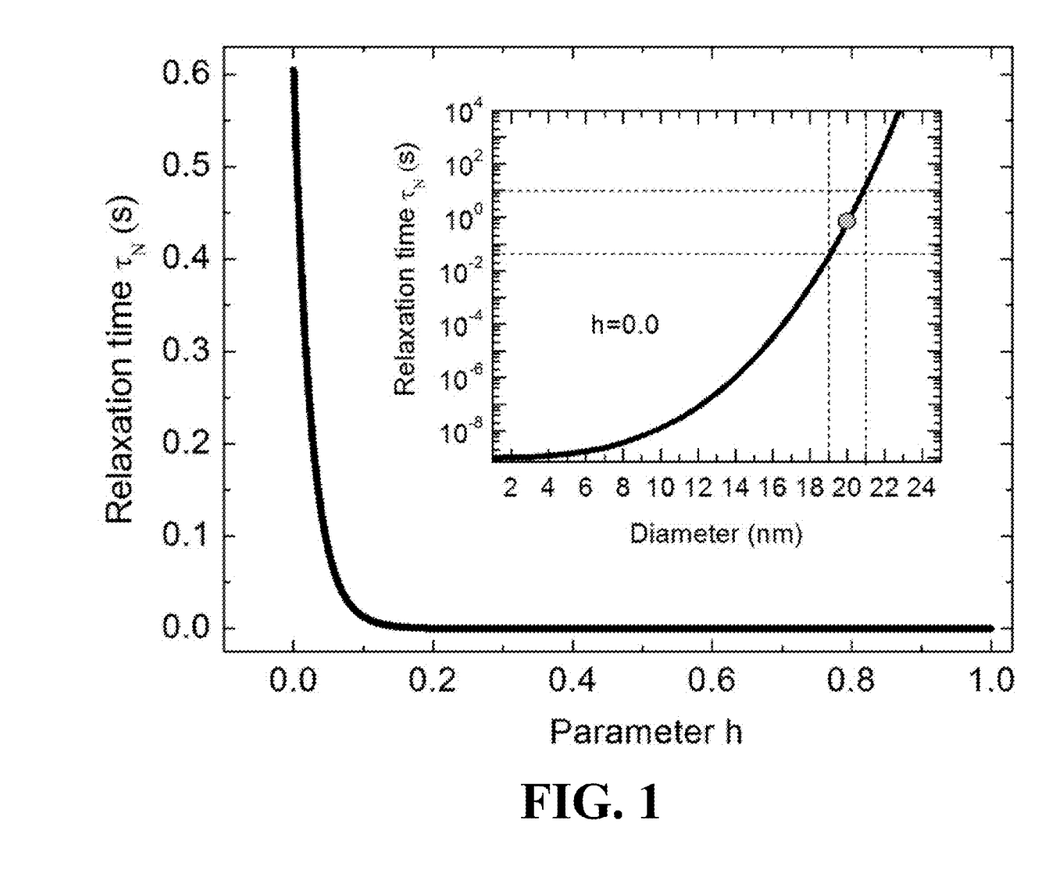
FIG. 1 depicts calculated Néel relaxation times plotted against a parameter $h=H/H_k$ of MNPs having a 20 nm diameter. The inset shows the Néel relaxation times vs. magnetic core diameter in zero field, h=0. Only MNPs of sizes between 19 nm and 21 nm produce observable decay signals.

In a time window of a typical magnetic relaxation measurement, e.g., a window having a time period between about 10 ms and about 10 s, only magnetic particles of a diameter between about 19 nm and about 21 nm contribute to a measurable decay signal. The relaxation time of these particles dramatically changes in a finite magnetic field (non-zero field, H>0). The characteristic Néel relaxation time plotted against parameter h for a sample including 20 nm MNPs is depicted in FIG. 1. The inset shows the Néel relaxation time plotted vs. MNP magnetic core diameter in zero field (H=0). The relaxation time is a maximum when the magnetic field is zero (H=0) and decreases rapidly as the parameter h increases. For example, the Néel relaxation time of 20 nm magnetic nanoparticles in a 200 µT field (HT=200µ corresponding to h~0.1 for MNPs having a 20 nm diameter) is 50 times shorter than its zero field value.

Suitable Objects and Bodies

Suitable objects for use in the method of the invention include, without limitation, any object into which or onto which magnetizable nano-particles can be distributed such as circuitry, fluid dynamic units, fluid distribution systems, or any other object capable of having MNPs distributed in or on and capable of being imaged using the instruments of this invention.

Suitable living organisms or bodies include, without limitation, any animal or plant into which or onto which MNPs can be distributed and capable of being imaged by the instruments of this inventions. Exemplary examples include, without limitation, bacterial, viruses, other microorganisms, humans, mammals, birds, fish, insects, amphibians, reptiles, or any other living organism.

Method

Figure 2A:
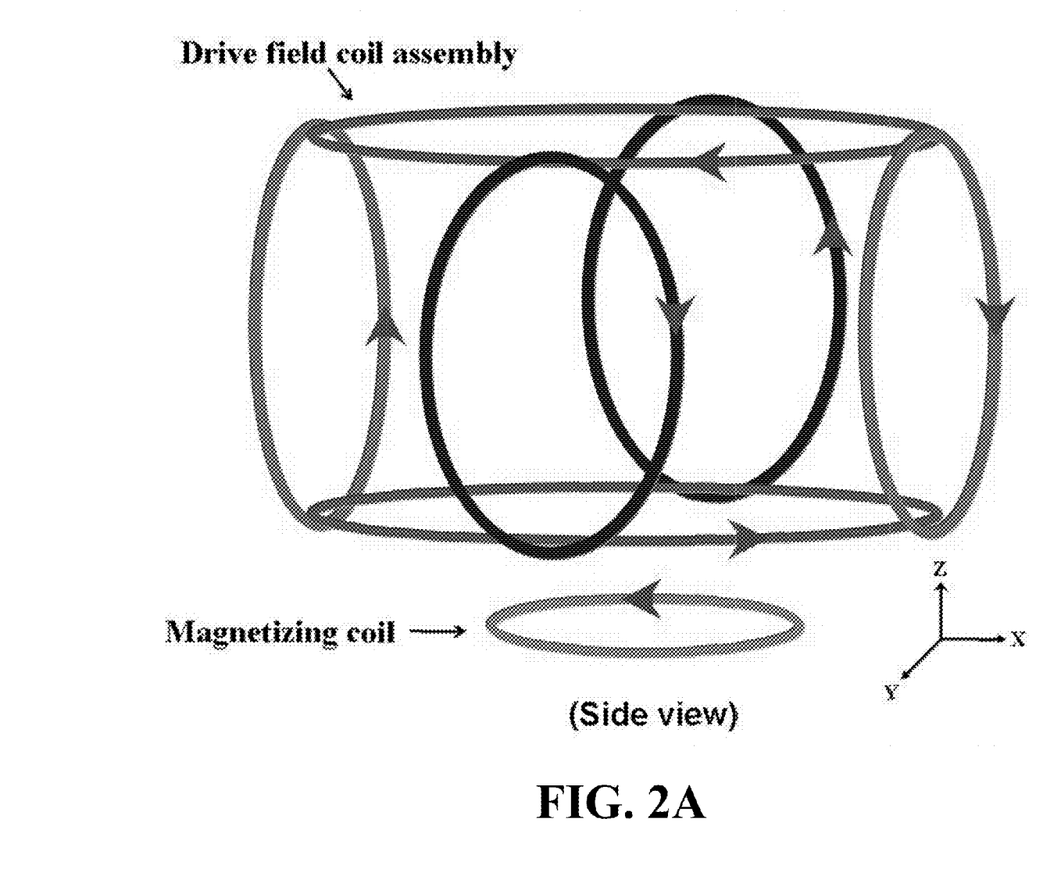
FIG. 2A depicts a schematic illustration of an embodiment of a drive coil assembly of this invention.
Figure 2B:
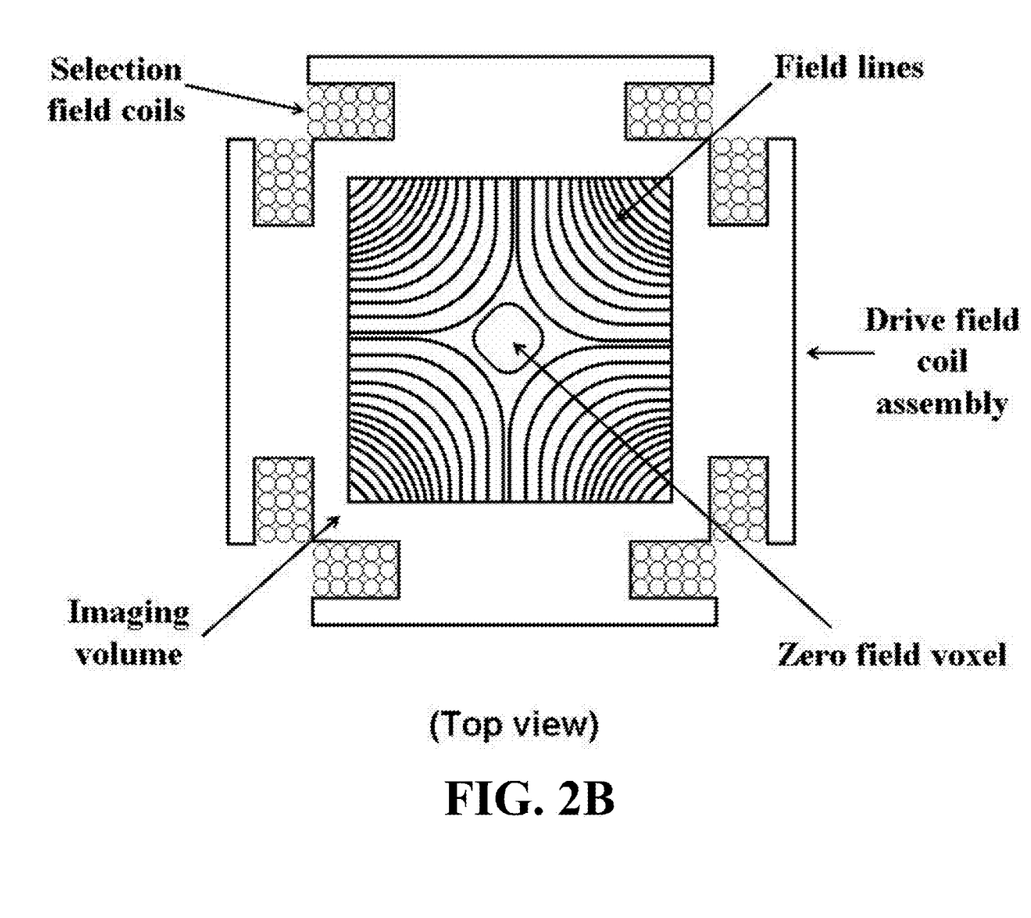
FIG. 2B depicts a top view of the drive coil assembly of FIG. 2A, where the coil assembly was constructed of polyacetal and oxygen-free copper wires.

To record an image, the object, body (living organism) or part thereo is placed in a selection magnetic field (static magnetic field) generated by three pairs of coil (drive coils) disposed in an orthogonal arrangement to each other as schematically illustrated in FIG. 2A. By a prudent choice of currents supplied to the drive coils, a zero field voxel (ZFV) is produced and can be positioned anywhere in the object, body (living organism) or part thereof, and especially at a region of interest (ROI) within the object, body (living organism) or part thereof. FIG. 2B illustrates the magnetic field distribution in the xy-plane, which vanishes in a center (the coils generate fields in opposite direction) of an imaging volume and increases towards the edges. After the magnetizing field $H_{mag}$ is switched off, MNPs located outside the ZFV relax in a finite field (H>0), so their magnetization decays rapidly, generally, within a few milliseconds and does not or substantially does not contribute measurably to a measured decay signal. For MNPs within the ZFV, their magnetization decay rate is slower and contributes most to the measured signal. The ZFV can be focused and/or positioned very accurately over a selected ROI either using mechanical scanning or by changing currents supplied to the drive coils.

In certain embodiments, mechanical scanning and current adjusting can be used in combination to focus and/or position the ZFV over a selected or desired ROI. Mechanical scanning is performed either by moving the whole drive coil assembly or by moving the body (living organism), object or part thereof within the drive coil assembly.

A 2D or 3D tomographic image of the magnetic tracer distribution in the ROI is directly obtained by mapping magnetization decays measured using a sensitive magnetic field sensor. Similar experimental coil arrangements developed for generating oscillating magnetic fields and moving a field free point have been used by others.

The signal detection of this invention is accomplished by using a single channel low $T_c$ SQUID system. The system is equipped with a dc-SQUID inductively coupled to a 12 mm pick-up coil configured as a first-order gradiometer with a baseline of 50 mm and is controlled by dc-SQUID electronics. The total field noise with the pick-up coil at 1 kHz is 20 fT/√Hz dominated by the environmental noise. The signal is digitized at 1 kHz using a 16-bit analog-to-digital converter available from National Instruments. The Labview® software interface is used for data acquisition, for controlling the drive field coils, and for magnetizing the magnetizing coil. After switching off the magnetizing field, the SQUID flux lock loop (FLL) is put into operation with a defined delay time. A delay in an acquisition time of 50 ms is chosen to suppress residual fields due to eddy currents generated in the magnetizing coil.

Figure 3A:
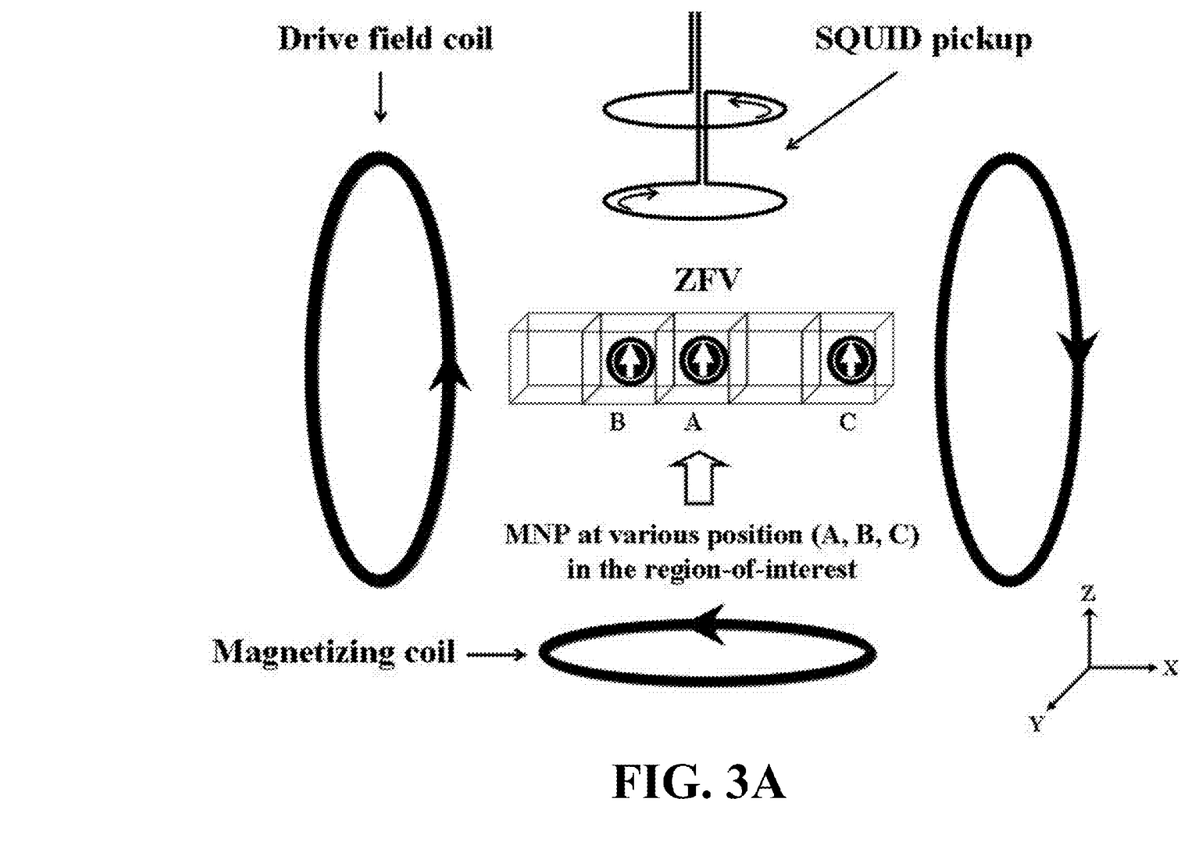
FIG. 3A depicts a schematic illustration of an embodiment of an instrument setup of this invention (only one pair of drive coils is shown, while the complete system includes three pairs of drive coils orthogonally oriented with respect to each other). MNPs are located at different positions (A, B, and C) inside the ROI.

The imaging capability is demonstrated using commercially available gamma-ferric oxide ($\gamma$-$Fe_2O_3$) magnetic nanoparticles. These particles are spherical in shape (average magnetic core diameter is about 20 nm), and superparamagnetic in nature. The magnetic particles are coated with Carboxyl to prevent agglomeration. The sample is mounted onto a non-magnetic sample holder, which is located on a center axis of the coil assembly. The major system components used in the imaging set-up are illustrated in FIG. 3A (only one pair of the coil is shown). Initially, the sample is exposed to a magnetizing field of amplitude close to the anisotropy field (i.e., $H_{mag}$~$H_K$). Such a field value is chosen to eliminate or minimize magnetizing effects on the relaxation behavior. In weak magnetizing fields, the characteristic relaxation time is equal to the magnetizing time, i.e., $t_c$=$t_{mag}$. In addition, this allows magnetic moments of MNPs to get saturated instantly (as fast as ~1 ns for h~1), which reduces the signal acquisition time.

Figure 3B:
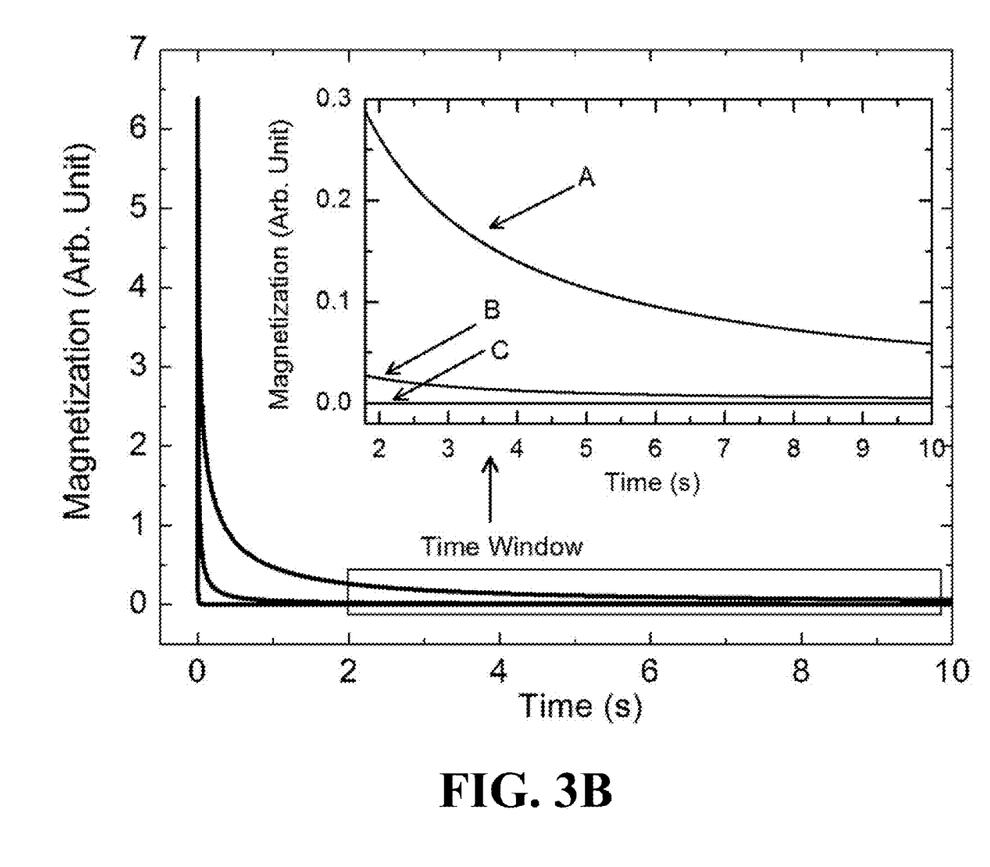
FIG. 3B depicts magnetic relaxation curves of MNPs located at different positions inside the ROI. Only MNPs in the ZFV (A) produce measurable decay signals in a time window between about 2 s and 10 s as shown in the inset.

FIG. 3B shows Néel relaxation plots of magnetic nanoparticles located inside and outside the ZFV (distributed along the x-axis in the ROI). MNPs located inside or positioned in the ZFV (position A) produce an observable response due to their longer relaxation times, whereas MNPs located outside the ZFV (position B and position C) generate very little response due to their shorter relaxation times. The MNPs located outside the ZFV relax faster after the magnetizing field $H_{mag}$ is switched off and, therefore, do not contribute or contribute substantially nothing to the decay signal in the measurement time window as can be seen in the inset of FIG. 3B.

The pulse duration is generally between about 0.1 seconds and 5 seconds. In certain embodiments, the pulse duration is between about 0.5 s and about 4 s. In other embodiments, the pulse duration is between about 0.5 s and about 3 s. In other embodiments, the pulse duration is between about 0.5 s and about 2 s. The magnetic field strength of the pulse field is generally between about 0.1 mT to about 100 mT. In certain embodiments, the magnetic field strength of the pulse field is generally between about 0.1 mT to about 50 mT. In certain embodiments, the magnetic field strength of the pulse field is generally between about 0.5 mT to about 25 mT. In certain embodiments, the magnetic field strength of the pulse field is generally between about 0.5 mT to about 10 mT. In certain embodiments, the magnetic field strength of the pulse field is generally between about 0.5 mT to about 5 mT. The selection field gradients is generally between about 0.1 mT/cm and about 50 mT/cm. In certain embodiments, the selection field gradient is between about 0.5 mT/cm and about 50 mT/cm. In certain embodiments, the selection field gradient is between about 0.5 mT/cm and about 25 mT/cm. In certain embodiments, the selection field gradient is between about 0.5 mT/cm and about 10 mT/cm. In certain embodiments, the selection field gradient is between about 0.5 mT/cm and about 5 mT/cm.

Reduction to Practice

Figure 4A:
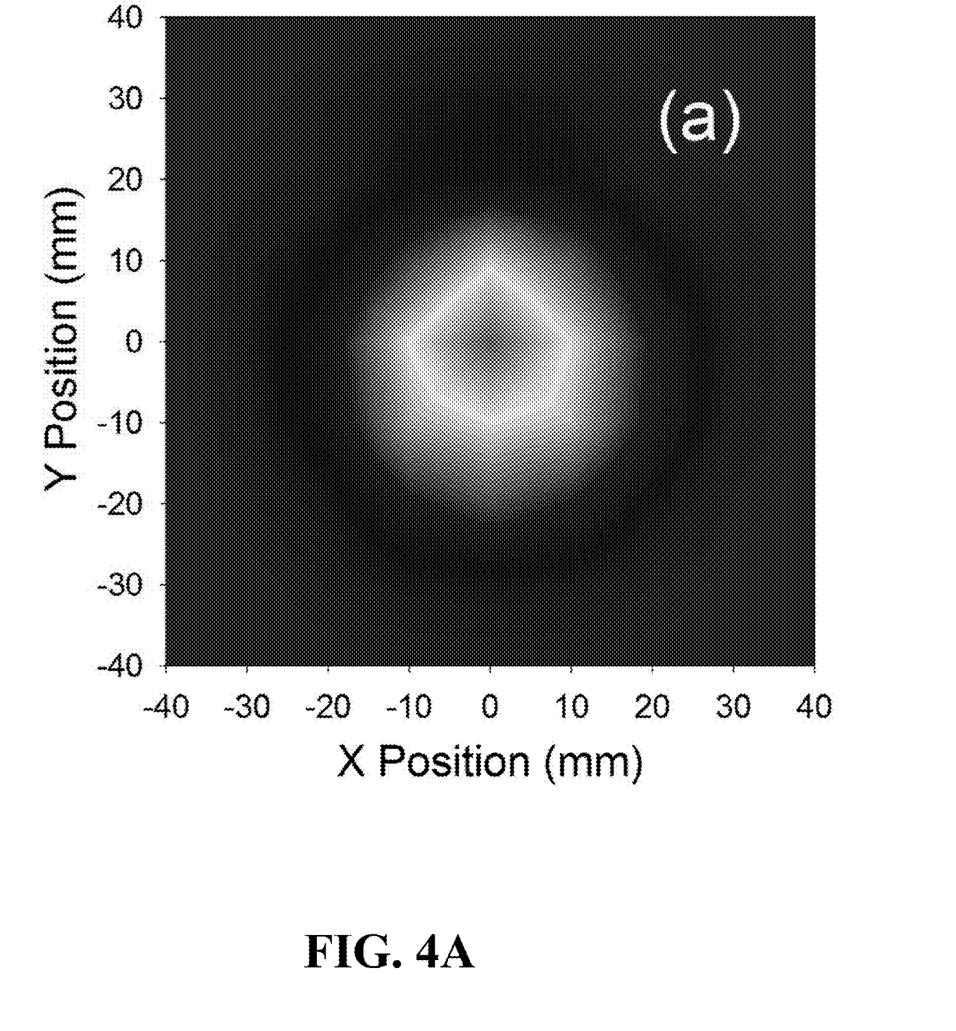
FIGS. 4A&B depicts the magnetic images of a MNP cluster measured at 20 mm above the cluster by a 12 mm SQUID gradiometer in a stray field (A) and using the technique of this invention (B). The planar sample has iron content of 200 nmol (~11.2 μg) located at x,y=0,0. The stray field image was recorded in a 2 mT dc field, where as the image was obtained by measuring the remanence flux in a selection field gradient of 1 mT/cm after applying 1 s magnetizing pulse of 2 mT.
Figure 4B:
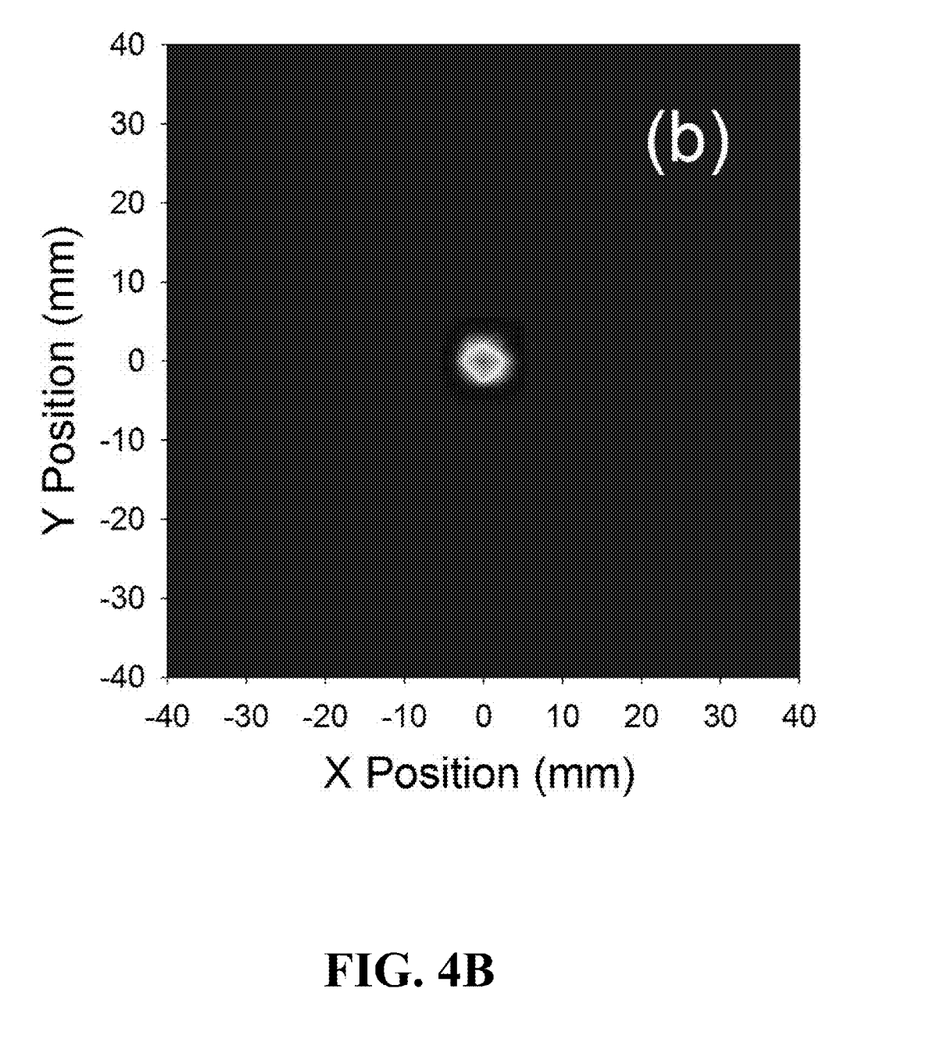

FIGS. 4A&B show magnetic images of a MNP cluster measured at 20 mm above the cluster by a 12 mm SQUID gradiometer in a stray field as shown in FIG. 4A and using the technique of this invention shown in FIG. 4B. The planar sample has an iron content of 200 nmol (~11.2 µg) located at x,y=0,0. The stray field image was recorded in a 2 mT dc field, *** whereas the image using the technique of this invention was obtained by measuring the remanence flux in a selection' field gradient of 1 mT/cm after a 1 s magnetizing pulse having a field strength of 2 mT. The image using the technique of this invention clearly shows an improved spatial resolution. The stray field image resolution strongly depends on the pick-up coil size and the sample-to-sensor distance, whereas the image using the technique of this invention has a spatial resolution that is not limited by the pick-up coil size or the sample-to-sensor distance. Moreover, employing larger pick-up coils can further improve the field sensitivity without sacrificing the spatial resolution.

We obtained a spatial resolution of 4 mm in our image of the $\gamma$-$Fe_2O_3$ magnetic nanoparticles at relatively large distance (20 mm) from the sensor in a magnetizing field of 2 mT (about 40% of saturation) using a field gradient of 1 mT/cm. The field gradient is limited by our current drive coil setup. However, the present methodology is amenable to higher gradients. The spatial resolution is inversely proportional to the magnetic field gradient. Using the values of K=2.7 kJ/m$^3$ and $M_S$=1.4×10$^6$ A/m, the anisotropy field $\mu_0 H_k$=3.9 mT is obtained. Assuming for h=$H_T$/$H_K$~0.5 the relaxation time decreases so the magnetization decays rapidly within few milliseconds and basically contributes no measurable signal inside the measurement time window, and a field gradient of 10 mT/cm, the spatial resolution can be theoretically predicted ~0.4 mm.

Figure 5:
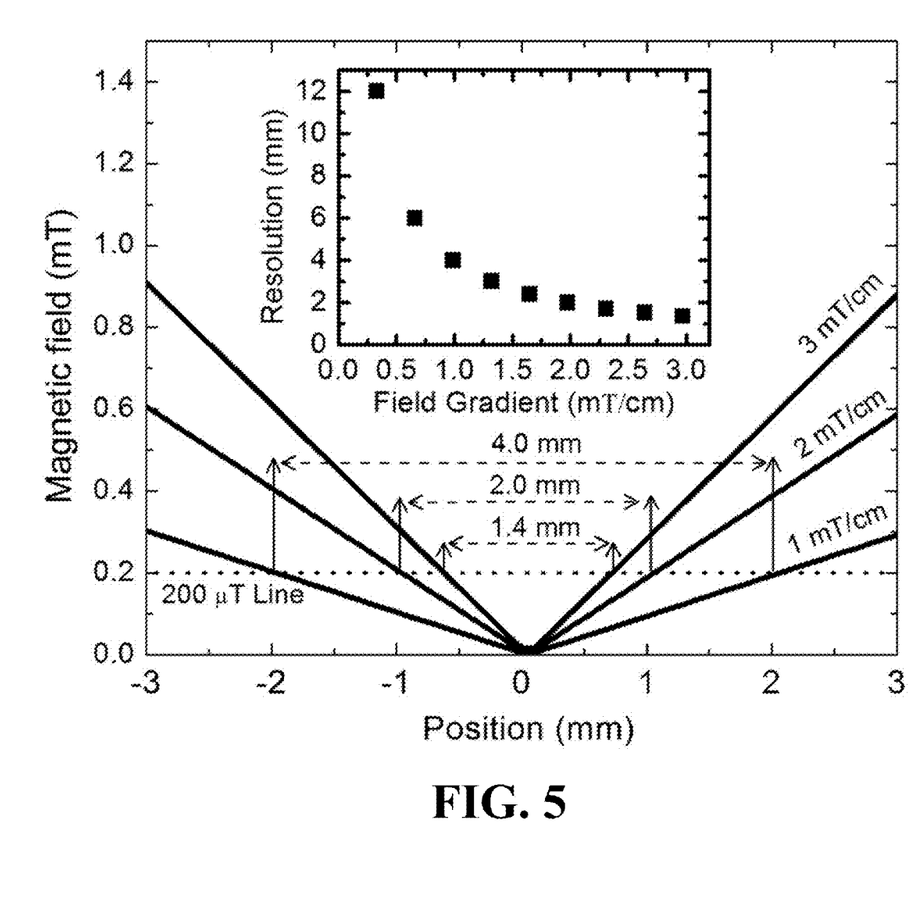
FIG. 5 depicts on-axis distribution profile of a magnetic field near the ZFV for three different selection field gradients (1 mT/cm, 2 mT/cm and 3 mT/cm). In a selection field of 200 μT, the lower limit of spatial resolution is less than 1.5 mm as shown in the insert.

Image spatial resolution can be further improved using higher field gradients as shown in FIG. 5. The spatial resolution is limited primarily by the size of the zero field voxel (ZFV), which directly depends on the magnetic field gradient value used in the selection field as shown in the inset of FIG. 5. The field gradient can be increased by either reducing a separation between the three pairs of drive coils, reducing imaging volume and/or increasing the drive currents. Suppression of environmental noise by passive/active shielding techniques and using higher order pickup gradiometers can also be used to increase detection sensitivity, which is limited by signal-to-noise ratio (SNR).

The signal acquisition time (temporal resolution) of the technique of this invention primarily depends on the Néel relaxation time of the MNPs, which largely depends on the size distribution fraction (monodispersity) of the MNPs. Recent progress in nanomaterials syntheses has proved that solution-phase syntheses are capable of producing monodisperse magnetic nanoparticles with controlled chemical and magnetic properties. Therefore, the acquisition time can be reduced sharply from a few seconds to a few micro seconds (µs) with optimized monodisperse MNPs. The delay in acquisition time can be reduced further using fast DC control switches based on MOSFET. Parallel imaging using multiple pickup coils and advanced sensitivity encoding imaging techniques (SENSE), where imaging time has been reduced without significant sacrifice in SNR, also can considerably enhance the performance of the imaging techniques of this invention. Larger ZFVs can also be used in cases where fast scanning is necessary.

Another important characteristic of the techniques of this invention is that they detect magnetic nanoparticles directly, unlike other imaging techniques such as contrast-enhanced MRI, which detect the nanoparticles indirectly. In MRI, signal intensity changes occur due to fast dephasing of proton spins caused by local susceptibility variation created by MNPs. The imaging of this invention operates at relatively low fields and, thus, the image resolution can be defined much below the saturation field of the MNPs unlikely the case of magnetic particle imaging (MPI), where the resolution depends on the nonlinear magnetization curve of the MNPs, which requires magnetic field above the saturation field.

MRX measurements have so far been performed using SQUID sensors. However recently Ludwig et al. reported on MRX measurements using two fluxgate magnetometers operated in a differential configuration. This differential arrangement increases the signal sensitivity compared to the single fluxgate setup by a factor of 2. Using the setup, the authors were able to detect magnetite $Fe_3O_4$ nanoparticles in aqueous solution down to about 1 μmol Fe. Likewise Chung et al. demonstrated the ac susceptibility technique as a tool for MRX measurement. In their biosensor scheme, the characteristic time scale of the MNPs can be determined directly by measuring the ac susceptibility as a function of time. The authors demonstrated that the peak in the imaginary part of the ac susceptibility shifts to lower frequencies upon binding target molecules to the MNPs due to the increase of their hydrodynamic diameter.

SUMMARY

We have developed a novel magnetic relaxation imaging method taking advantage of the non-linear behavior of the characteristic time scale of the Néel relaxation of magnetized nanoparticles, when measured in a selection field. The image of this invention is obtained by scanning the magnetization decay of MNPs measured by a remote SQUID sensor. Magnetic relaxation images obtained in an unshielded environment show significantly improved spatial resolution over stray field images for superparamagnetic iron oxide particles. Due to the high sensitivity of SQUID detection and the strong large magnetic response generated by optimized superparamagnetic nanoparticles, we expect the technique of this invention to be of great importance in developing novel medical diagnostic instruments suitable for non-invasive detection and characterization of vulnerable plaque.

The instruments for implementing the methods of this invention includes at least 4 major parts: (1) one hardware coil or a plurality of hardware coils, 2) a SQUID and other associated electronics, 3) a magnetic field scanner, and 4) a software interface and image processing tools. The instrument can be useful for early identification and noninvasive monitoring of plaque inflammation in vivo by imaging the accumulation of MNPs within macrophages in vulnerable plaques. Because it does not require immobilization of the target or separation of unbound markers, the method and instruments of this invention can provide more accurate results. Since no radiation is involved and the quantity of injected magnetic nanoparticles can be orders of magnitude below tolerance level, the instrument may be able to provide useful images of sufficient quality to detect and quantify initiation and progression of monocyte recruitment into atherosclerotic plaques. The instrument is not only capable of generating direct images of magnetic nanoparticle agglomerates by measuring magnetic flux at fixed magnetic field gradient after saturation, but also is capable of distinguishing between bound and unbound magnetic labels.

Various payloads of biomolecules, pharmacological and imaging agents can be administered systematically to local regions of interest (e.g., cancer or atherosclerotic lesions). Delivery methods and intracellular uptake mechanisms of nanoparticle carriers have been described in the literature.

All references cited herein are incorporated by reference. The foregoing disclosure and description of the invention are illustrative and explanatory. Various changes in the size, shape, and materials, as well as in the details of the illustrative construction may be made without departing from the spirit of the invention as described above and claimed hereafter.

We claim:

1. A method for imaging a region of interest in an object, a living organism or part thereof comprising:
   administering magnetic nanoparticles (MNPs) to the object, living organism or part thereof so that a portion of the MNPs are distributed within a region of interest (ROI) or a plurality of ROIs therein;
   placing the object, living organism or part thereof in a selection magnetic field generated by a drive coil assembly comprising three pairs of orthogonally arranged drive coils;
   supplying currents to the drive coils to form a zero field voxel (ZFV);
   positioning the ZFV at one or more of the ROIs;
   magnetizing the MNPs in the one or more ROIs with a magnetic field pulse generated by a magnetizing coil;
   switching the selection magnetic field off, and
   detecting magnetization decay rates of the MNPs via a sensitive magnetic field sensor assembly capable of distinguishing between bound and unbound MNPs within the ROIs,
   where the magnetic field pulse has a duration of between about 0.1 seconds and 5 seconds, where MNPs located inside or positioned in the ZFV produce an observable response due to their longer relaxation times, where MNPs located outside the ZFV have relaxation times of milliseconds (ms) and make no measurable contribution to the observable response, and where the relaxations are due to Néel and Brownian relaxations.

2. The method of claim 1, further comprising:
   acquiring magnetization decays due to Néel and Brownian relaxation of the MNPs that depend on a magnetization in the one or more ROIs influenced by the positioning of the ZFV, and
   evaluating the magnetization decays to determine changes in a spatial distribution of the MNPs in the one or more ROIs.

3. The method of claim 1, further comprising:
   prior to the magnetizing step, focusing the ZFV over the one or more ROIs; and
   after the detecting step, mapping the detected magnetization decays to form a 2D or 3D tomographic image of a MNP distribution in the one or more ROIs.

4. The method of claim 3, wherein the 2D or 3D tomographic image is formed by directly measuring a magnetic flux at a fixed magnetic field gradient after MNP saturation.

5. The method of claim 3, wherein the focusing comprises:
   mechanical scanning the ZFV over the one or more ROIs by moving the drive coil assembly and/or by moving the object, living organism or part thereof within the drive coil assembly.

6. The method of claim 3, wherein the focusing comprises:
   changing the currents supplied to the drive coils of the drive coil assembly.

7. The method of claim 3, wherein the focusing comprises:
   mechanical scanning the ZFV over the one or more ROIs by moving the whole drive coil assembly and/or by moving the object or living organism within the drive coil assembly, and
   changing the currents supplied to the drive coils of the drive coil assembly.

8. The method of claim 1, wherein the sensitive magnetic field sensor assembly comprises one sensitive magnetic field sensor or a plurality of sensitive magnetic field sensor.

9. The method of claim 8, wherein the plurality of sensitive magnetic field sensors are arranged in a pattern.

10. The method of claim 9, wherein signals induced in the sensor pattern by temporal changes in the magnetization decays in the ZFV are received and are analyzed to obtain a spatial distribution of the MNPs in the one or more ROIs.

11. The method of claim 8, wherein the sensitive magnetic field sensors comprise superconducting quantum interference devices (SQUIDs).

12. The method of claim 1, further comprising:
    evaluating the magnetization decays to determine moments of the MNPs in the one or more ROIs.

* * * * *